US00PP32612P2

(12) United States Plant Patent
Scheys

(10) Patent No.: US PP32,612 P2
(45) Date of Patent: Dec. 8, 2020

(54) ***HEUCHERA* PLANT NAMED 'HAPPY FLAMES'**

(50) Latin Name: *Heuchera* hybrid
Varietal Denomination: Happy Flames

(71) Applicant: Diederik Alexander Maria Scheys, Réty (FR)

(72) Inventor: Diederik Alexander Maria Scheys, Réty (FR)

( * ) Notice: Subject to any disclaimer, the term of this patent is extended or adjusted under 35 U.S.C. 154(b) by 0 days.

(21) Appl. No.: 16/602,544

(22) Filed: Oct. 24, 2019

(51) Int. Cl.
*A01H 5/12* (2018.01)
*A01H 6/14* (2018.01)

(52) U.S. Cl.
USPC ..... Plt./440

(58) Field of Classification Search
USPC ..... Plt./440, 250, 311, 413

CPC ... A01H 5/02; A01H 5/12; A01H 6/80; A01H 6/14

See application file for complete search history.

(56) References Cited

PUBLICATIONS

Ashtree Nursery New Varieties for 2018 retrieved on Apr. 20, 2020, retrieved from the Internet at http://www.ashtreenursery.co.uk/wp-content/uploads/2017/04/Ashtree-flyer-January-2018.pdf, 2 pp. (Year: 2018).*

* cited by examiner

*Primary Examiner* — June Hwu
(74) *Attorney, Agent, or Firm* — Penny J. Aguirre

(57) ABSTRACT

A new cultivar of *Heuchera* named 'Happy Flames' that is characterized by its leaves that are green-yellow in color with red veins with the red veins more prominent in spring, its high sun tolerance, its vigorous growth habit, its dense plant habit and its flowers that are white in color.

2 Drawing Sheets

Botanical classification: *Heuchera* hybrid.
Cultivar designation: 'Happy Flames'.

CROSS REFERENCE TO A RELATED APPLICATIONS

This application is related to a European plant breeders' rights application filed on Dec. 19, 2017, application No. 2017/3334. There have been no offers for sale anywhere in the world prior to the effective filing date of this Application and no accessibility to one of ordinary skill in the art could have been derived from the printed plant breeder's rights documents. This application is co-pending with a U.S. Plant Patent Application filed for a plant derived from the same breeding program that is entitled *Heuchera* Plant Named 'Happy Moon' (U.S. Plant Patent pending)*.
*(Applicant gives the examiner the authority to replace the U.S. Plant Patent pending with an Application No. or Patent No. if applicable and delete this statement.)

BACKGROUND OF THE INVENTION

The present invention relates to a new and distinct cultivar of *Heuchera* of hybrid origin, botanically known as *Heuchera* 'Happy Flames' and is hereinafter referred to by its cultivar name 'Happy Flames'.

The new cultivar was discovered as a chance seedling in a container by the Inventor in Réty, France in July of 2015. The source of the seedling was from seed collected in 2009 from open pollinated plants in a trial field that contained numerous proprietary *Heuchera* seedlings from the Inventor's breeding program and other cultivars. The parentage of 'Happy Flames' is therefore unknown.

Asexual propagation of the new cultivar was first accomplished under the direction of the Inventor by tissue culture initiated from meristem tissue in March of 2018 in Beervelde, Belgium. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Happy Flames' as a new and unique cultivar of *Heuchera*.

1. 'Happy Flames' exhibits leaves that are green-yellow in color with red veins with the red veins more prominent in spring.
2. 'Happy Flames' exhibits a high sun tolerance.
3. 'Happy Flames' exhibits a vigorous growth habit.
4. 'Happy Flames' exhibits a dense plant habit.
5. 'Happy Flames' exhibits flowers that are white in color.

'Happy Flames' can be most closely compared to the *Heuchera* cultivars 'Delta Dawn' (U.S. Plant Pat. No. 23,545), 'Red Lightning' (U.S. Plant Pat. No. 27,767) and 'Happy Moon'. All three are similar to 'Happy Flames' in foliage coloration. 'Delta Dawn' differs from 'Happy Flames' in having a less dense plant habit, leaves that are less sun resistant, shorter flower stem's and leaves that are less glossy. 'Red Lightning' differs from 'Happy Flames' in having a less dense plant habit, and leaves that are less sun resistant, smaller in size and less glossy. 'Happy Moon' differs from 'Happy Flames' in having a foliage that is lighter green and more yellow in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but are not limited to website disclosures by Pioneer Seeds, RHS Gardening, Denis plants, and Pépinére des DEUX CAPS.

BRIEF DESCRIPTION OF THE DRAWINGS

The accompanying colored photograph illustrates the overall appearance and distinct characteristics of the new *Heuchera*. The photograph was taken of a plant 18 months in age as grown outdoors in a 15-cm container in Attenhove, Belgium.

The photograph in FIG. 1 provides a side view of the plant of 'Happy Flames' in bloom.

Figure 1:
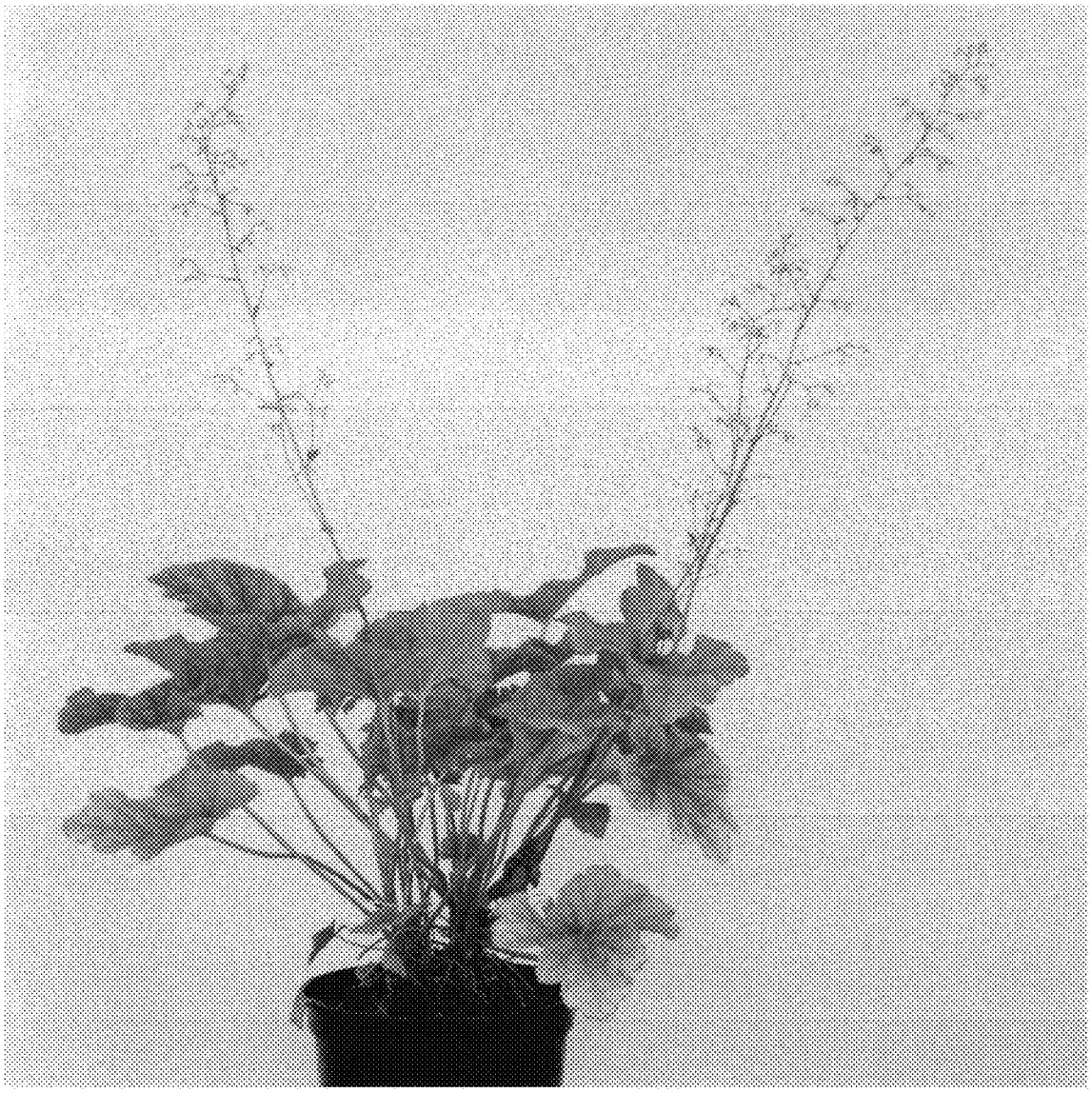
Figure 2:
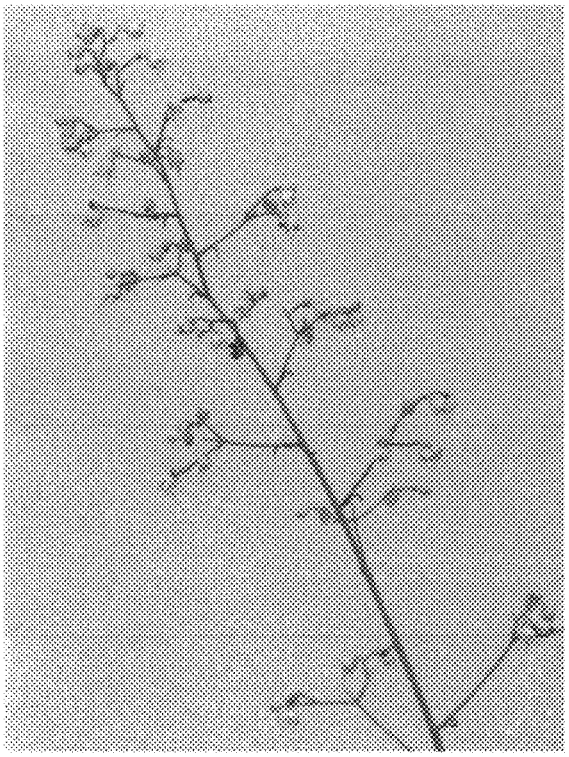

The photograph in FIG. 2 provides a close up of the inflorescence of 'Happy Flames'.

Figure 3:
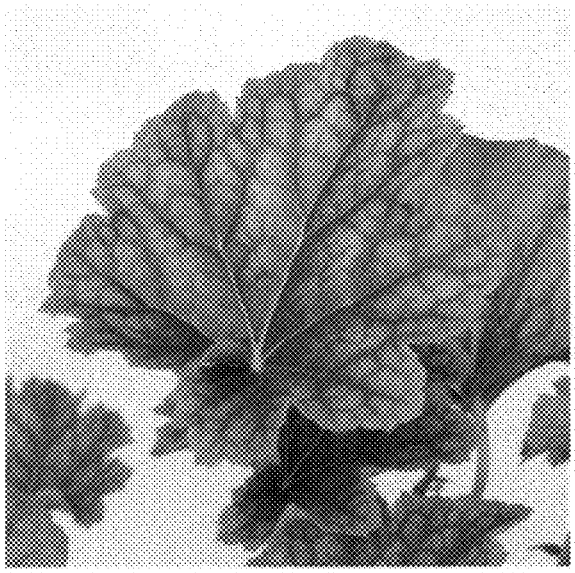
Figure 4:
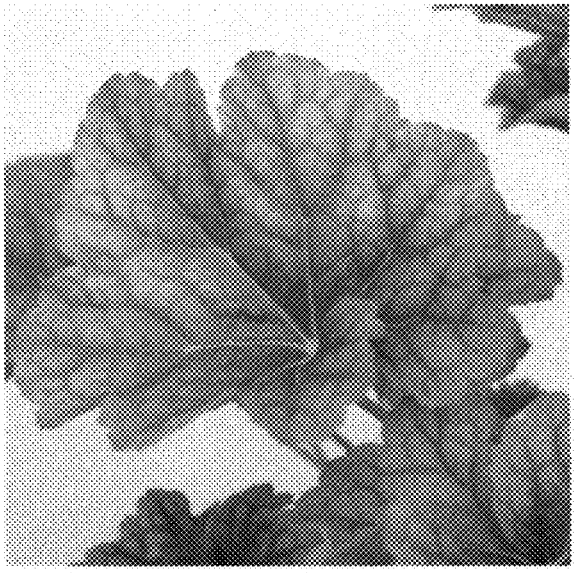

The photograph in FIG. 3 and FIG. 4 provide close up view of the foliage of 'Happy Flames' with FIG. 3 taken of a young leave and FIG. 4 taken of a mature leaf.

The colors in the photograph are as close as possible with the digital photography techniques available, the color values cited in the detailed botanical description accurately describe the colors of the new *Heuchera.*

DETAILED BOTANICAL DESCRIPTION OF THE PLANT

The following is a detailed description of 18 month-old plants of the new cultivar as grown outdoors in 15-cm containers Attenhove, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

- *Blooming period*.—Late spring into summer in Belgium.
- *Plant type*.—Herbaceous perennial.
- *Plant habit*.—Flattened globular with inflorescences held above the foliage.
- *Height and spread*.—An average of 26.5 cm in height (soil level to top of foliar plane), average of 53.9 cm in height (soil level to top of floral plane) and 47.8 cm in spread.
- *Hardiness*.—At least in U.S.D.A. Zones 3 to 9.
- *Environmental stress*.—Tolerant to high sun exposure.
- *Diseases and pests*.—No susceptibility or resistance to pests or diseases has been observed.
- *Root description*.—Fibrous roots on woody rootstalks, 158D in color.
- *Propagation*.—Tissue culture.
- *Root development*.—An average of 8 weeks to fully develop from a tissue culture plug in a 7-cm when planted April through August in Belgium.
- *Growth rate*.—Vigorous.

Stem description (base of leaves):

- *Shape*.—Round.
- *Stem color*.—Young; 187B to 187C, mature; N200A.
- *Stem size*.—An average of 0.9 mm in diameter and 4.5 cm in length.
- *Stem strength*.—Strong.
- *Stem aspect*.—Upright.
- *Stem surface*.—Glabrous, consisting of old leaf-bases.
- *Stem number*.—Average of 5.
- *Branching habit*.—Stems emerge from basal rosette, no lateral branches.

Foliage description:

- *Leaf shape*.—Broad ovate to near orbicular.
- *Leaf division*.—Simple.
- *Leaf base*.—Hastate, lobes touching to slightly overlapping.
- *Leaf apex*.—Short and abruptly acute.
- *Leaf venation*.—Laciniate, upper surface 151B, lower surface 150C.
- *Leaf margins*.—Crenate with abruptly acute tips on each tooth.
- *Leaf attachment*.—Petiolate.
- *Leaf arrangement*.—Alternate in basal rosettes.
- *Leaf lobes*.—Lobed, an average of 7 lobes, occasionally 9, shallow in depth, divergent.
- *Leaf surface*.—Both surfaces non-rugose, smooth and pubescent, moderately to densely covered with very short strigose hairs an average of 0.5 mm in length and too small to measure color, upper surface very slightly glossy, lower surface matte.
- *Leaf color*.—Young upper surface; N34A and 179A, margins 149A, young lower surface; 181A to 181B, margins 145B and 149B, mature upper surface; N199C to N199D, margins 151B to 151C, mature lower surface; 177D, margins 150B and 151D, fall and winter color similar to mature foliage until browning.
- *Leaf size*.—An average of 11.3 cm in length and 10.1 cm in width.
- *Leaf quantity*.—An average of 8 per basal rosette.
- *Petioles*.—An average of 16.1 cm in length and 3 mm in diameter, moderate strength, both surfaces glossy, upper surface color N144A, changing to 176A at the tip, lower surface color N144A to N144B, changing to 176C to 176D at the tip.
- *Stipules*.—Leafy stipule at the base of each leaf, average length 1.5 cm, average width 4 mm, acute tip, 187D in color.
- *Internode length*.—Average of 2 mm.

Flower description:

- *Inflorescence type*.—Numerous small bell-shaped flowers arranged on panicles on peduncles emerging from a basal rosette.
- *Inflorescence size*.—An average of 37.1 cm in height and 7.1 cm in diameter.
- *Inflorescence number*.—An average of 3.
- *Flower fragrance*.—None.
- *Flower quantity*.—Average of 120 flowers per flowering stem.
- *Flower lastingness*.—Average of one week.

*Flower buds*.—Obovate in shape, an average of 3 mm in length and 2 mm in diameter, color; 151C and tinged 179A at the top, surface is matte and densely covered with very short glandular hairs; an average of 0.2 mm in length and too small to measure color.

*Flower aspect*.—Outward and nodding.

*Flower type*.—Single, campanulate.

*Flower size*.—Average of 6 mm in height and diameter, 7 mm in length.

*Petals*.—Average of 5, rotate arrangement and implanted in the hypanthium at base, oblanceolate in shape, margin is entire, apex is acute, base is narrow attenuate, upper and lower surface is glabrous, smooth and matte, an average of 4 cm in length and 1 mm in width, color when opening upper and lower surface; a color between 69D and N155B, color when fully open upper and lower surface; a color between N155B and NN155D.

*Calyx*.—Campanulate, sepals fused to hypanthium, 5 mm in length and diameter.

*Sepals*.—An average of 5, lower 50% fused into campanulate hypanthium, short oblong in shape, an average of 4 mm in length and 1.25 mm in width, margin is entire and fused into hypanthium, apex is bluntly acute to obtuse, color; when opening and fully open upper surface 150D top 179B, when opening and fully open lower surface 151C, top 179A both surfaces are matte and densely covered with very short glandular hairs an average of 0.2 mm in length and to small to measure color.

*Peduncle*.—An average of 49.9 cm in length and 2 mm in diameter, 151B to 151C in color, primary flower aspect 40°, secondary peduncle aspect to main peduncle 60°, moderate in strength, surface moderately glossy and densely covered with very short soft glandular hairs; average of 0.2 mm in length and too small to measure color.

*Pedicels*.—An average of 2 mm in length and 0.5 mm in diameter, 153B in color, primary flower aspect straight on top of secondary pedicel, secondary and tertiary flower aspect is 45°, moderate in strength, surface matte and densely covered with very short soft glandular hairs; average of 0.2 mm in length and to small too measure color.

Reproductive organs:

*Gynoecium*.—Pistils; 2, 3.5 mm in length, stigma; club-shaped, 157D in color, 0.2 mm in diameter, style; an average of 3.8 mm in length and 157D in color, ovary; 150D in color.

*Androecium*.—Stamens; 5, anthers; triangular in shape, average of 0.5 mm in length and width, 199C in color, filament; 2 mm in length and NN155D in color, pollen; low in quantity and 156B in color.

*Seed/fruit*.—No fruit or seeds were observed to date.

It is claimed:

1. A new and distinct cultivar of *Heuchera* plant named 'Happy Flames' as herein illustrated and described.

* * * * *